(12) United States Patent
Katakura

(10) Patent No.: US 9,949,622 B2
(45) Date of Patent: Apr. 24, 2018

(54) ENDOSCOPE SYSTEM FOR GENERATING A COMPOSITE IMAGE FROM OPTICAL IMAGES OF DIFFERENT FOCUS

(71) Applicant: OLYMPUS CORPORATION, Hachioji-shi, Tokyo (JP)

(72) Inventor: Masahiro Katakura, Chofu (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/342,414

(22) Filed: Nov. 3, 2016

(65) Prior Publication Data

US 2017/0049306 A1 Feb. 23, 2017

Related U.S. Application Data

(63) Continuation of application No. PCT/JP2015/085050, filed on Dec. 15, 2015.

(30) Foreign Application Priority Data

Feb. 17, 2015 (JP) .................................. 2015-028436

(51) Int. Cl.
*A61B 1/04* (2006.01)
*A61B 1/00* (2006.01)
(Continued)

(52) U.S. Cl.
CPC ...... *A61B 1/00193* (2013.01); *A61B 1/00009* (2013.01); *A61B 1/00096* (2013.01);
(Continued)

(58) Field of Classification Search
CPC ............ A61B 1/00009; A61B 1/00188; A61B 1/00096; A61B 1/05; G02B 23/243;
(Continued)

(56) References Cited

U.S. PATENT DOCUMENTS

| 2012/0033105 A1* | 2/2012 | Yoshino | A61B 1/00009 |
| | | | 348/239 |
| 2013/0041221 A1* | 2/2013 | McDowall | A61B 1/00096 |
| | | | 600/111 |

(Continued)

FOREIGN PATENT DOCUMENTS

| JP | 4226235 B2 | 2/2009 |
| JP | 5593004 B2 | 9/2014 |
| WO | 2013061819 A1 | 5/2013 |

OTHER PUBLICATIONS

International Search Report (ISR) and Written Opinion dated Mar. 15, 2016 issued in International Application No. PCT/JP2015/085050.

(Continued)

*Primary Examiner* — John P Leubecker
(74) *Attorney, Agent, or Firm* — Holtz, Holtz & Volek PC

(57) ABSTRACT

An endoscope system includes an objective optical system OBL, an optical path splitting unit which splits an object image acquired by the objective optical system OBL into two optical images having a different focus, an image pickup element which acquires the optical images, and an image synthesis processing section which selects in a predetermined area an image with a relatively high contrast from the two optical images acquired, and generates a composite image, wherein the objective optical system OBL includes a first lens L1 having a negative refractive power which is nearest to object, and the endoscope system satisfies the following conditional expressions (1) and (2).

$$3 < D\_diff/im\_pitch \leq 100 \quad (1)$$

$$0.005 < D\_diff/R1\_r < 1.0 \quad (2)$$

where,
D_diff denotes an air conversion length of a difference in length of optical paths of the two optical images, (Continued)

im_pitch denotes a pixel pitch of the image pickup element, and $R1\_r$ denotes a radius of curvature at an image-side surface of the first lens having a negative refractive power.

4 Claims, 11 Drawing Sheets

(51) Int. Cl.
    *G02B 13/04*     (2006.01)
    *G02B 17/04*     (2006.01)
    *G02B 23/24*     (2006.01)
    *G02B 23/04*     (2006.01)
    *A61B 1/05*     (2006.01)
    *G02B 5/04*     (2006.01)

(52) U.S. Cl.
    CPC ...... *A61B 1/00186* (2013.01); *A61B 1/00188* (2013.01); *A61B 1/04* (2013.01); *A61B 1/051* (2013.01); *G02B 13/04* (2013.01); *G02B 17/04* (2013.01); *G02B 23/04* (2013.01); *G02B 23/24* (2013.01); *G02B 23/243* (2013.01); *G02B 23/2415* (2013.01); *G02B 23/2484* (2013.01); *G02B 5/04* (2013.01)

(58) Field of Classification Search
    CPC ................ G02B 23/2423; G02B 23/04; G02B 23/2484; H04N 2005/2255
    See application file for complete search history.

(56) References Cited

U.S. PATENT DOCUMENTS

| | | | |
|---|---|---|---|
| 2013/0217965 A1* | 8/2013 | Sasamoto | G02B 7/08 600/109 |
| 2013/0235174 A1* | 9/2013 | Namii | G03B 11/00 348/65 |
| 2013/0271587 A1 | 10/2013 | Tsuyuki | |
| 2013/0335534 A1* | 12/2013 | Hanzawa | H04N 5/23212 348/50 |
| 2014/0176692 A1 | 6/2014 | Tsuyuki et al. | |
| 2014/0198194 A1* | 7/2014 | Suga | G02B 23/243 348/65 |
| 2015/0042773 A1* | 2/2015 | Uzawa | A61B 1/00096 348/65 |

OTHER PUBLICATIONS

International Preliminary Report on Patentability (IPRP) dated Aug. 31, 2017 issued in counterpart International Application No. PCT/JP2015/085050.

* cited by examiner 435.84 — · — · —
656.27 · · · · · · · ·
587.56 ————

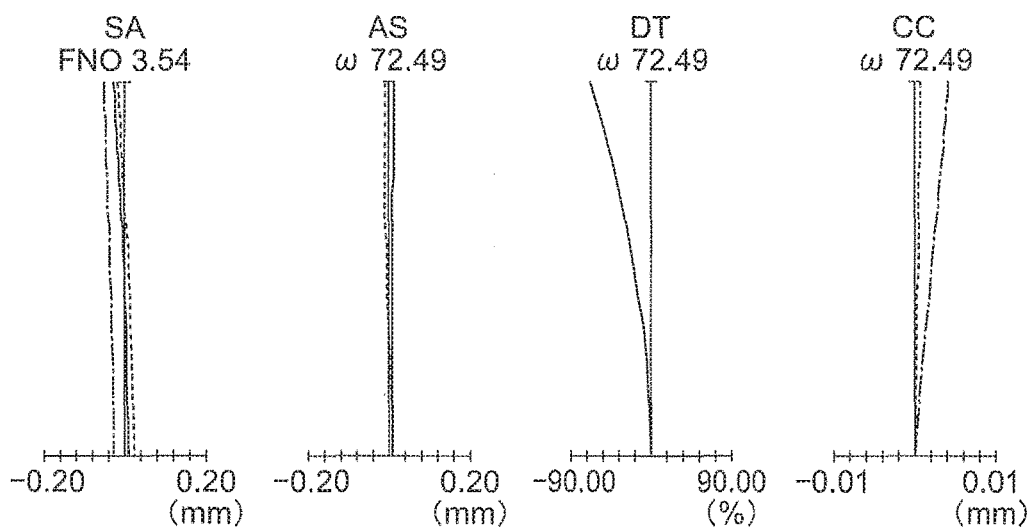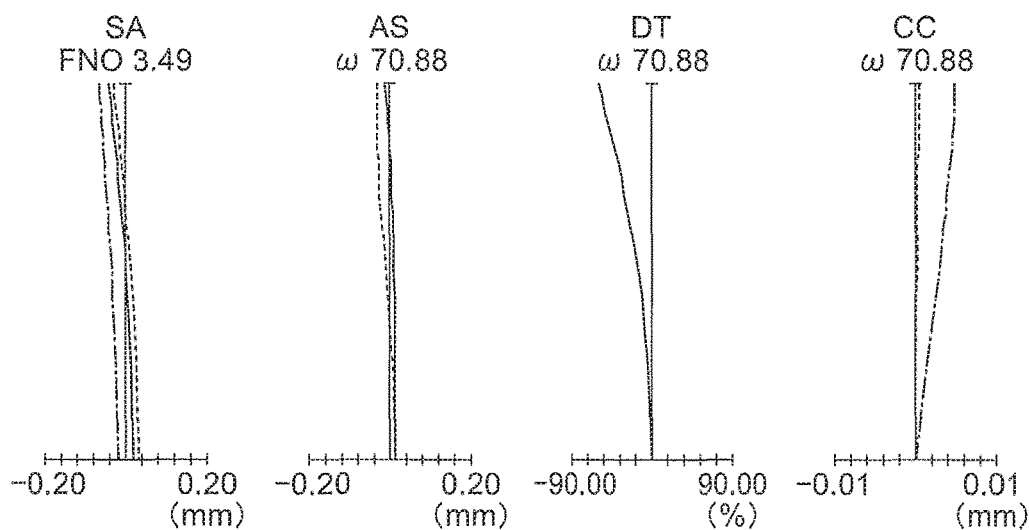

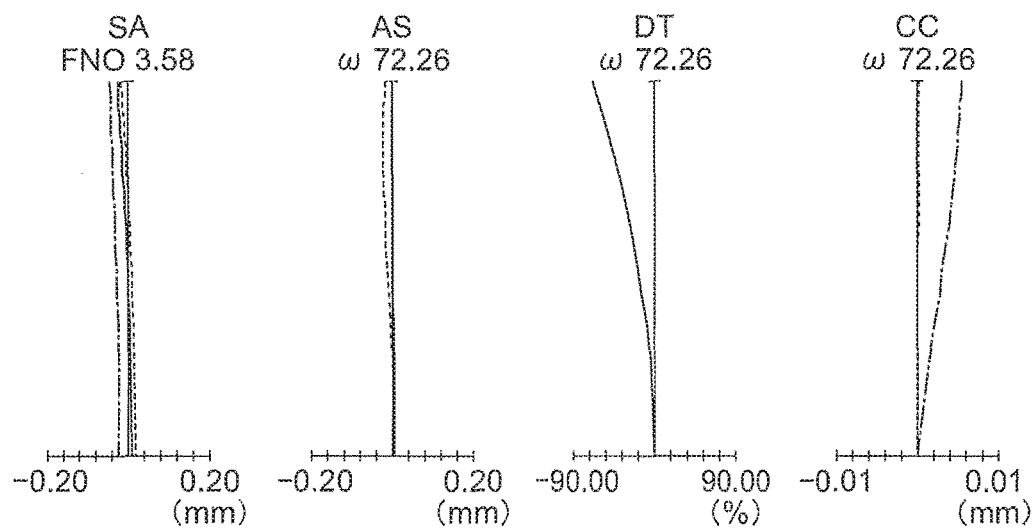
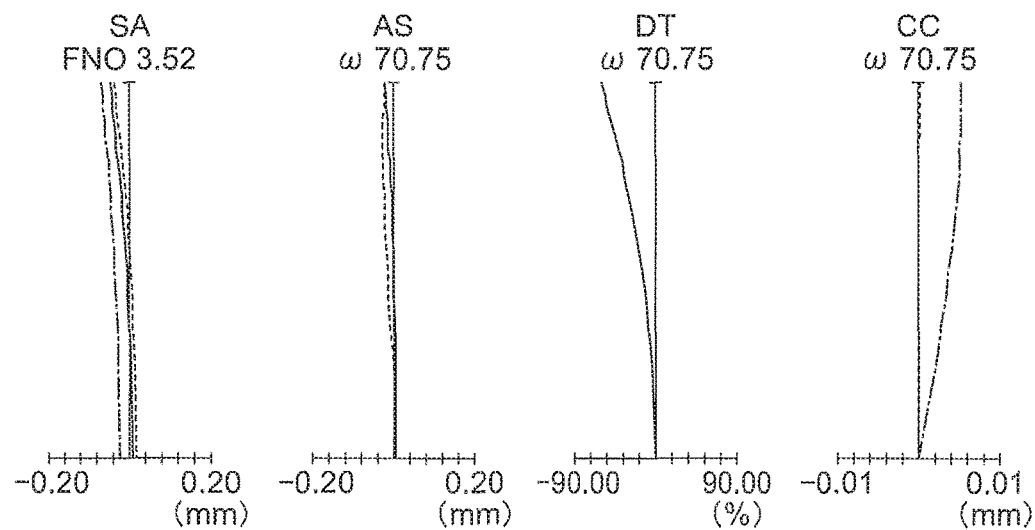

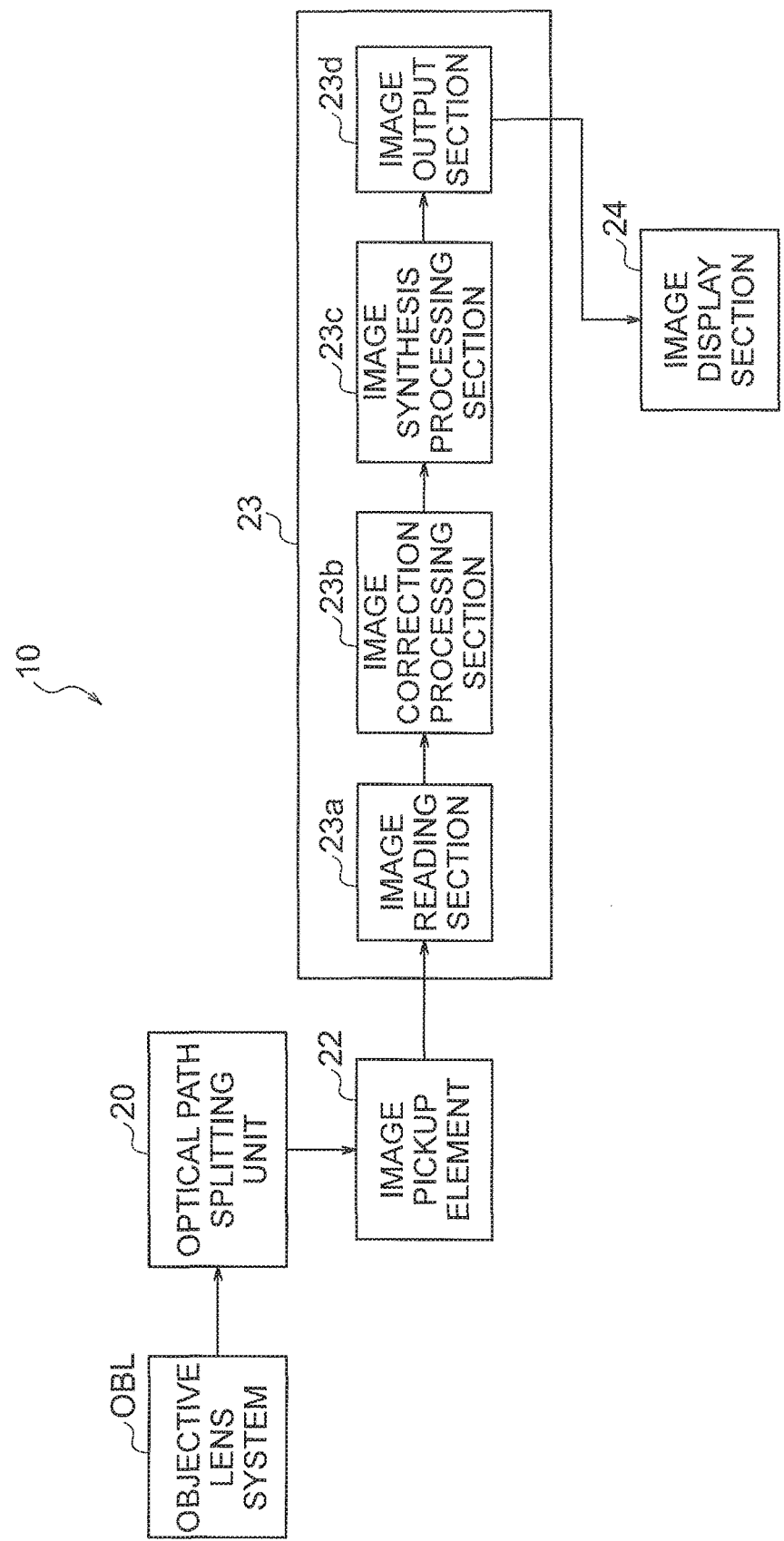

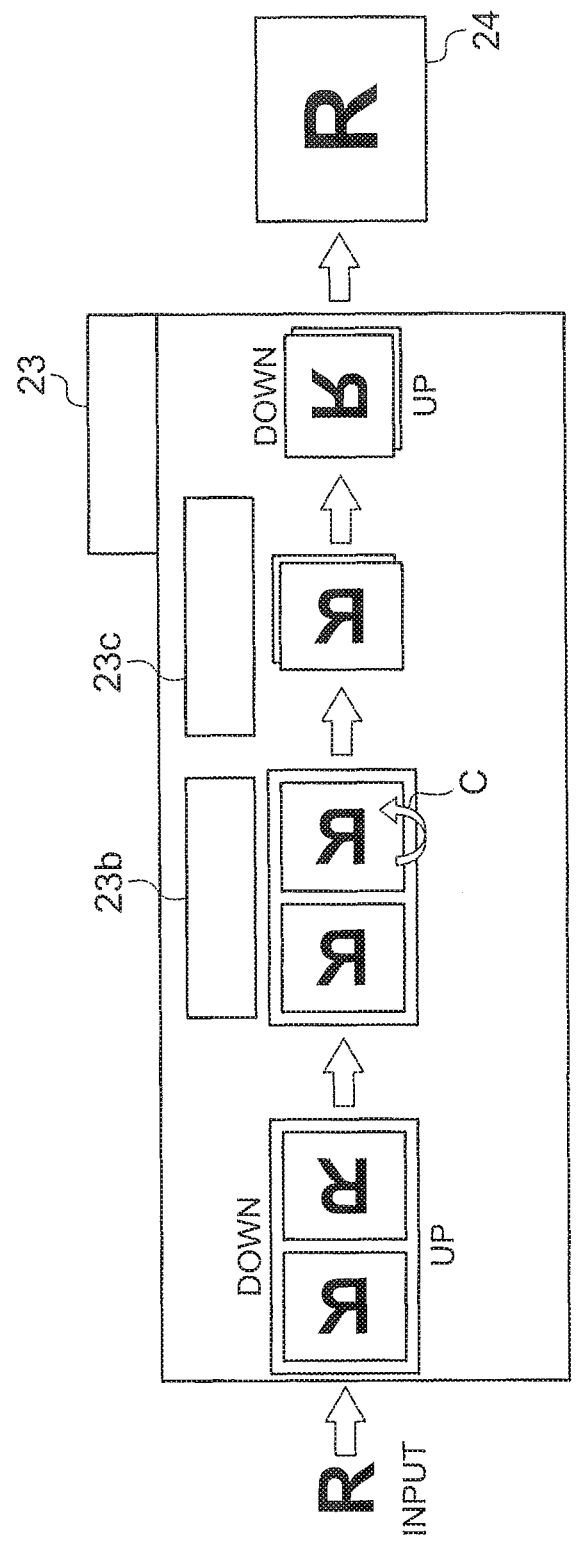

ENDOSCOPE SYSTEM FOR GENERATING A COMPOSITE IMAGE FROM OPTICAL IMAGES OF DIFFERENT FOCUS

CROSS-REFERENCE TO RELATED APPLICATION

The present application is a continuation application of PCT/JP2015/085050 filed on Dec. 15, 2015 which is based upon and claims the benefit of priority from Japanese Patent Application No. 2015-028436 filed on Feb. 17, 2015; the entire contents of which are incorporated herein by reference.

BACKGROUND OF THE INVENTION

Field of the Invention

The present invention relates to an endoscope system, and particularly to a depth-of-field endoscope system.

Description of the Related Art

Generally, in equipment provided with an image pickup element, such as an endoscope system, a depth of field has been known to become narrow with the number of pixels of the image pickup element becoming large. In other words, in an image pickup element, when a pixel pitch (horizontal and vertical dimensions of one pixel) is made small, since a permissible circle of confusion becomes small with the pixel pitch made small, the depth of field of an image pickup apparatus becomes narrow.

For widening the depth of field, in Japanese Patent Publication No. 4226235 for example, an arrangement in which, images are formed by splitting a self-image, and the images acquired are combined by image processing and the depth is widened has been disclosed. Moreover, in Japanese Patent Publication No. 5593004, an arrangement in which, images are formed by dividing a self-portrait, and the images acquired are combined by image processing and the depth is widened has been disclosed. In this arrangement, since it is possible to acquire images by using one image pickup element, it is outstanding from a cost point of view.

SUMMARY OF THE INVENTION

The present invention provides the following means.

An endoscope system according to an aspect of the present invention includes an objective optical system, an optical path splitting unit which splits an object image acquired by the objective optical system into two optical images of a different focus, an image pickup element which acquires the optical images, and an image synthesis processing section which selects in a predetermined area, an image with a relatively high contrast out of the two optical images acquired, and generates a composite image, wherein the objective optical system includes a first lens having a negative refractive power which is nearest to object, and the endoscope system satisfies the following conditional expressions (1) and (2).

$$3 < D\_diff/im\_pitch \leq 100 \quad (1)$$

$$0.005 < D\_diff/R1\_r < 1.0 \quad (2)$$

where,

D_diff denotes an air conversion length of a difference in length of optical paths of the two optical images, im_pitch denotes a pixel pitch of the image pickup element, and R1_r denotes a radius of curvature at an image-side surface of the first lens having a negative refractive power.

BRIEF DESCRIPTION OF THE DRAWINGS

FIG. 2A is a cross-sectional view in a normal observation state and FIG. 2B is a cross-sectional view in a close observation state;

FIG. 4A is a cross-sectional view in a normal observation state and FIG. 4B is a cross-sectional view in a close observation state;

FIG. 5A, FIG. 5B, FIG. 5C, and FIG. 5D are aberration diagrams showing a spherical aberration (SA), an astigmatism (AS), a distortion (DT), and a chromatic aberration of magnification (CC) respectively in the normal observation state of the example 2, and FIG. 5E, FIG. 5F, FIG. 5G, and FIG. 5H are aberration diagrams showing a spherical aberration (SA), an astigmatism (AS), a distortion (DT), and a chromatic aberration of magnification (CC) respectively in the close observation state of the example 2;

FIG. 6A is a cross-sectional view in a normal observation state and FIG. 6B is a cross-sectional view in a close observation state;

FIG. 7A, FIG. 7B, FIG. 7C, and FIG. 7D are aberration diagrams showing a spherical aberration (SA), an astigmatism (AS), a distortion (DT), and a chromatic aberration of magnification (CC) respectively in the normal observation state of the example 3, and FIG. 7E, FIG. 7F, FIG. 7G, and FIG. 7H are aberration diagrams showing a spherical aberration (SA), an astigmatism (AS), a distortion (DT), and a chromatic aberration of magnification (CC) respectively in the close observation state of the example 3;

FIG. 8 is a functional block diagram showing a configuration of an endoscope system according to an embodiment of the present invention;

FIG. 12 is a diagram showing an image formation state when an image is formed on the image pickup element after odd number of reflections by a beam splitter in the endoscope system according to the embodiment of the present invention.

DETAILED DESCRIPTION OF THE INVENTION

Figure 1:
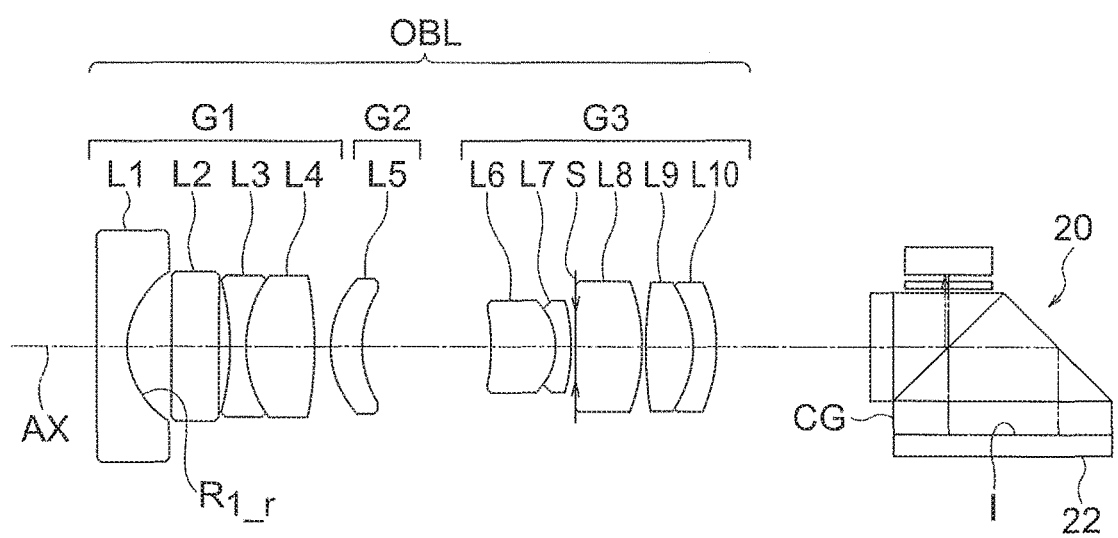
FIG. 1 is a diagram showing a cross-sectional arrangement of an objective optical system, an optical path splitting unit, and an image pickup element in an endoscope system according to an embodiment of the present invention.

Reasons for adopting such arrangements and effects thereof in an endoscope system according to the present embodiment will be described below by referring to the accompanying diagrams. However, the present invention is not limited to the embodiments described below.

The endoscope system according to the present embodiment includes an objective optical system, an optical path splitting unit which splits an object image acquired by the objective optical system into two optical images of a different focus; an image pickup element which acquires the optical images, and an image synthesis processing section which selects in a predetermined area, an image with a relatively high contrast from the two optical images acquired, and generates a composite image, wherein the objective optical system includes a first lens having a negative refractive power which is nearest to object, and the endoscope system satisfies the following conditional expressions (1) and (2).

$$3 < D\_diff/im\_pitch \leq 100 \quad (1)$$

$$0.005 < D\_diff/R1\_r < 1.0 \quad (2)$$

where,

D_diff denotes an air conversion length of a difference in length of optical paths of the two optical images, im_pitch denotes a pixel pitch of the image pickup element, and R1_r denotes a radius of curvature at an image-side surface of the first lens having a negative refractive power.

By acquiring two optical images of different focus and generating a composite image, it is possible to achieve an image with a wide depth of field. For splitting an optical path, it is necessary to dispose an optical member such as a prism unit. Therefore, it is necessary to make a distance (FB) from a rearmost surface of the objective optical system up to an image forming position longer than that in a normal optical system.

By using a lens having a negative refractive power for the first lens of the objective optical system, since it is possible to achieve a long FB with lesser number of lenses, it is preferable.

Conditional expression (1) regulates an appropriate focus difference of two optical images with different focus. When conditional expression (1) is satisfied, it is possible to maintain the appropriate focus difference. Consequently, it is possible to acquire a favorable image while widening the depth of field.

When an upper limit value of conditional expression (1) is exceeded, the focus difference in the two optical images becomes excessively large. Consequently, even when a composite image of two optical images is generated, since an object distance at which the image is out of focus exists, it is not preferable.

When a value falls below a lower limit value of conditional expression (1), the focus difference in the two optical images becomes excessively small. Consequently, since an effect of widening the depth of field is diminished, it is not preferable.

Conditional expression (2) regulates an appropriate relationship of the focus difference in the two optical images and the first lens having a negative refractive power.

When an upper limit value of conditional expression (2) is exceeded, an amount of an off-axis aberration that occurs in the first lens having a negative refractive power becomes large. Consequently, since an image quality is degraded in a periphery of image, it is not preferable.

When a value falls below a lower limit value of conditional expression (2), the power (refractive power) of the first lens having a negative refractive power becomes small. Consequently, it is not possible to achieve the necessary FB, and therefore it is not preferable.

It is desirable to satisfy the following conditional expression (1)' instead of conditional expression (1).

$$20 < D\_diff/im\_pitch < 60 \quad (1)'$$

Furthermore, it is more desirable to satisfy the following conditional expression (1)" instead of conditional expression (1).

$$25 < D\_diff/im\_pitch < 45 \quad (1)''$$

It is desirable to satisfy the following conditional expression (2)' instead of conditional expression (2).

$$0.020 < D\_diff/R1\_r < 0.1 \quad (2)'$$

Furthermore, it is more desirable to satisfy the following conditional expression (2") instead of conditional expression (2).

$$0.025 < D\_diff/R1\_r < 0.045 \quad (2)''$$

Moreover, according to a preferable aspect of the present invention, it is desirable to satisfy the following conditional expressions (3) and (4).

$$-0.05 < D\_diff/R1\_f < 0.05 \quad (3)$$

$$-1.0 < D\_diff/FL\_L01 < -0.005 \quad (4)$$

where,

D_diff denotes the air conversion length of the difference in length of optical paths of the two optical images, R1_f denotes a radius of curvature at an object-side surface of the first lens having a negative refractive power, and FL_L01 denotes a focal length of the first lens at e-line.

Conditional expressions (3) and (4) regulate an appropriate relationship of the focus difference of the two optical images respectively, and the first lens having a negative refractive power.

When either an upper limit value of conditional expression (3) is exceeded or a value falls below a lower limit value of conditional expression (3), the radius of curvature of a first surface of the lens becomes excessively small, and water removal is degraded. Accordingly, since an image becomes such that the focus is partially blurred where water droplets are accumulated, it is not preferable.

When a value falls below a lower limit value of conditional expression (4), an amount of an off-axis aberration that occurs in the first lens having a negative refractive power becomes large. Consequently, since an image quality is degraded in a peripheral area, it is not preferable.

When an upper limit value of conditional expression (4) is exceeded, the power of the first lens having a negative refractive power becomes excessively small. Consequently, since it is not possible to achieve the necessary FB, it is not preferable.

It is desirable to satisfy the following conditional expression (3)' instead of conditional expression (3).

$$-0.005 < D\_diff/R1\_f < 0.005 \qquad (3)'$$

Furthermore, it is more desirable to satisfy the following conditional expression (3)" instead of conditional expression (3).

$$-0.001 < D\_diff/R1\_f < 0.001 \qquad (3)''$$

It is desirable to satisfy the following conditional expression (4)' instead of conditional expression (4).

$$-0.8 < D\_diff/FL\_L01 < -0.02 \qquad (4)'$$

Furthermore, it is more desirable to satisfy the following conditional expression (4)" instead of conditional expression (4).

$$-0.4 < D\_diff/FL\_L01 < -0.03 \qquad (4)''$$

Moreover, according to a preferable aspect of the present invention, it is desirable to satisfy the following conditional expressions (5) and (6).

$$0.01 < D\_diff/fw < 2.0 \qquad (5)$$

$$0.002 < D\_diff/FB < 0.05 \qquad (6)$$

where,

D_diff denotes the air conversion length of a difference in length of optical paths of the two optical images, fw denotes a focal length of the objective optical system, and FB denotes an air conversion length from a rearmost lens of the objective optical system up to an image forming position.

Conditional expression (5) regulates an appropriate relationship of the focus difference in the two optical images of different focus and the focal length of the objective optical system.

When conditional expression (5) is satisfied, the two images have the appropriate focus difference. Consequently, it is possible to achieve a favorable image while widening the depth of field.

When an upper limit value of conditional expression (5) is exceeded, the focus difference in the two images becomes excessively large. Accordingly, even when a composite image of two optical images is generated, since a distance of an object at which the focus is blurred exists, it is not preferable.

When a value falls below a lower limit value of conditional expression (5), the focus difference in the two images becomes excessively small. Accordingly, since an effect of widening the depth of field is small, it is not preferable.

Conditional expression (6) regulates an appropriate ratio of the focus difference of the optical images and FB.

When an upper limit value of conditional expression (6) is exceeded, FB becomes excessively short. Consequently, since there is no space for disposing an optical element that splits an optical path, it is not preferable.

When a value falls below a lower limit value of conditional expression (6), FB becomes remarkably and excessively long. As a result, it is necessary to make the refractive power of the first lens remarkably large, and since mainly an off-axis aberration occurs, it is not preferable.

It is desirable to satisfy the following conditional expression (5)' instead of conditional expression (5).

$$0.03 < D\_diff/fw < 1.0 \qquad (5)'$$

Furthermore, it is more desirable to satisfy the following conditional expression (5)" instead of conditional expression (5).

$$0.045 < D\_diff/fw < 0.75 \qquad (5)''$$

It is desirable to satisfy the following conditional expression (6)' instead of conditional expression (6).

$$0.005 < D\_diff/FB < 0.02 \qquad (6)'$$

Furthermore, it is more desirable to satisfy the following conditional expression (6)" instead of conditional expression (6).

$$0.008 < D\_diff/FB < 0.014 \qquad (6)''$$

Moreover, according to a preferable aspect of the present invention, it is desirable that the objective optical system enables normal observation and close observation by driving a lens at an interior of the objective optical system, and satisfies the following conditional expression (7).

$$1.01 < \omega(w)/\omega(t) < 2.0 \qquad (7)$$

where, $\omega(w)$ denotes a half angle of view at the time of normal observation of the objective optical system, and $\omega(t)$ denotes a half angle of view at the time of close observation of the objective optical system.

Conditional expression (7) regulates an appropriate ratio of a change in an angle of view of the objective optical system.

When the objective optical system satisfies conditional expression (7), in the two optical images of different focus, the normal observation and the close observation are possible even while widening the depth of field. Particularly, since the magnification becomes large in the close observation, the depth of field tends to become small. Here, by using an image synthesis technology that will be described later, in the close observation, it is possible to make the depth of field small.

When a value falls below a lower limit value of conditional expression (7), the close observation is not possible. Consequently, the technology as in the present embodiment is not necessary.

When an upper limit value of conditional expression (7) is exceeded, the change in the angle of view becomes excessively large. Consequently, a lens diameter is enlarged, and a QOL (Quality Of Life) of patient is degraded, and therefore it is not preferable.

It is desirable to satisfy the following conditional expression (7)' instead of conditional expression (7).

$$1.02 < \omega(w)/\omega(t) < 1.5 \qquad (7)'$$

Furthermore, it is more desirable to satisfy the following conditional expression (7)" instead of conditional expression (7).

$$1.03 < \omega(w)/\omega(t) < 1.1 \qquad (7)''$$

Example 1

Next, an objective optical system in an endoscope system according to an example 1 of the present invention will be described below.

Figure 2A:
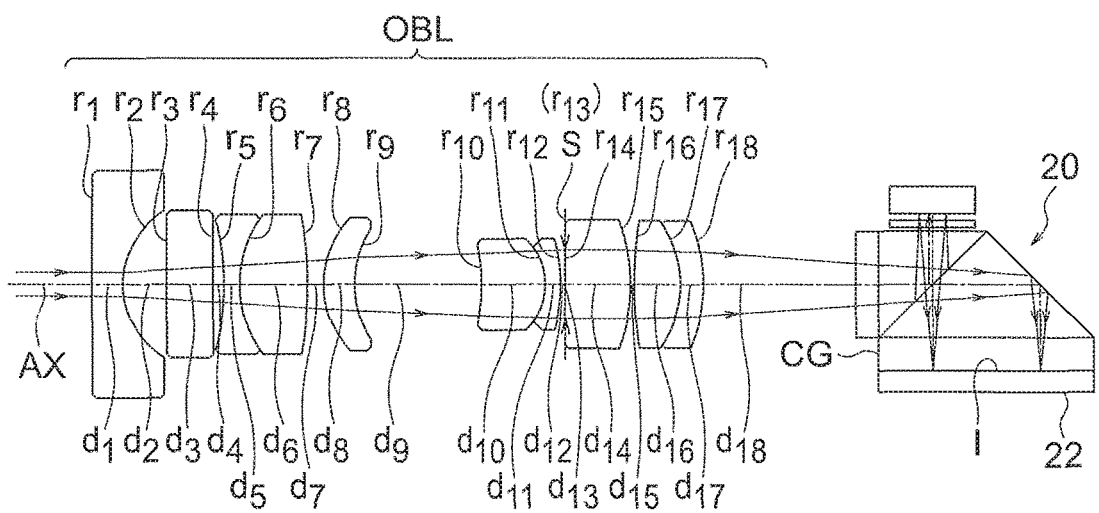
FIG. 2A and FIG. 2B are diagrams showing a cross-sectional arrangement of an objective optical system, an optical path splitting unit, and an image pickup element in an endoscope system according to an example 1 of the present invention, where.
Figure 2B:
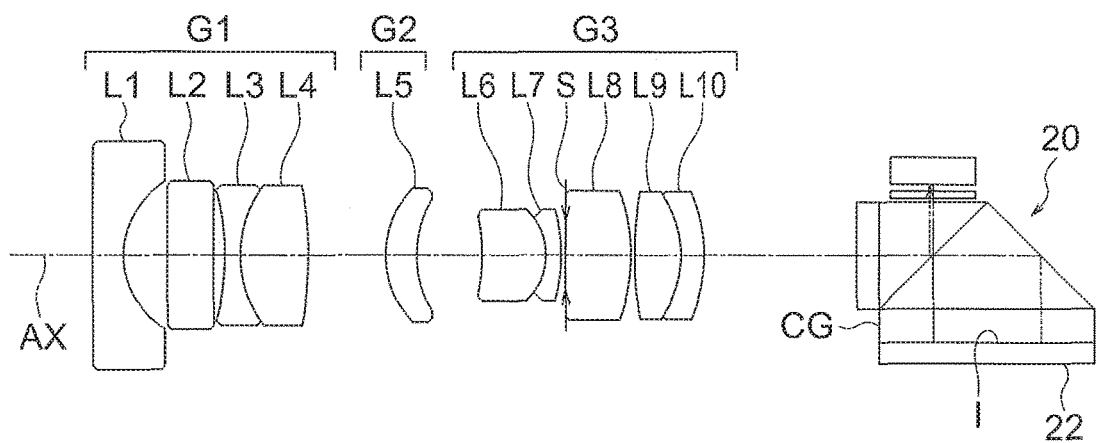
Figures 3A, 3B, 3C, 3D:
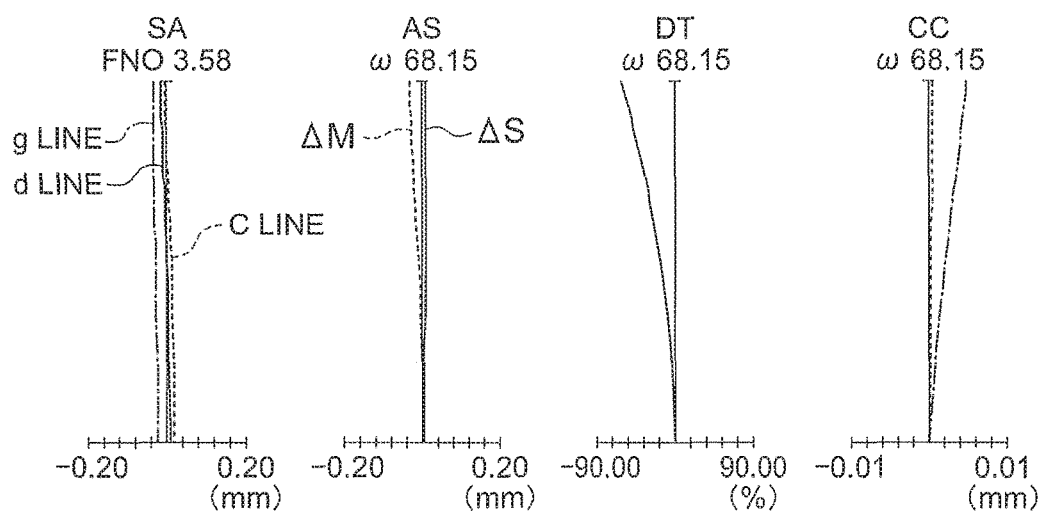
FIG. 3A, FIG. 3B, FIG. 3C, and FIG. 3D are aberration diagrams showing a spherical aberration (SA), an astigmatism (AS), a distortion (DT), and a chromatic aberration of magnification (CC) respectively in the normal observation state of the example 1.
Figures 3E, 3F, 3G, 3H:
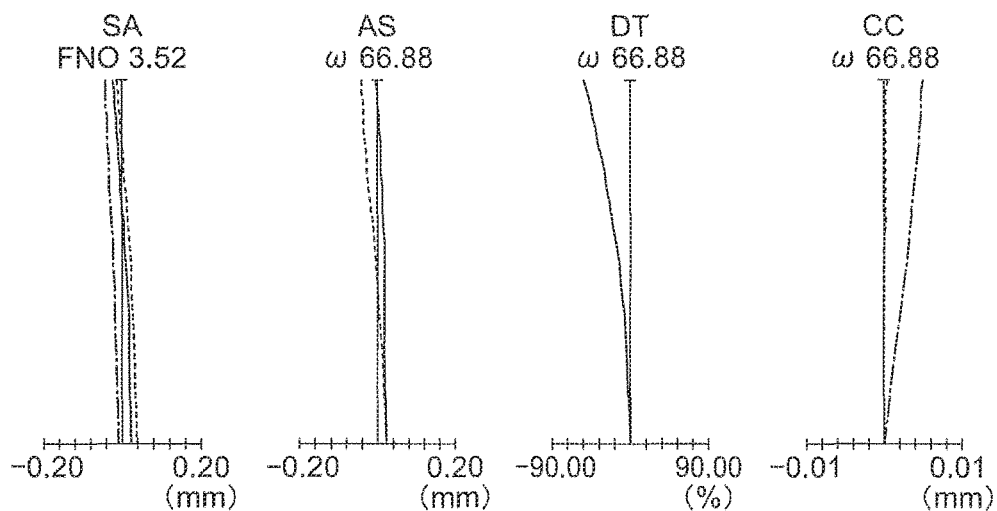
FIG. 3E, FIG. 3F, FIG. 3G, and FIG. 3H are aberration diagrams showing a spherical aberration (SA), an astigmatism (AS), a distortion (DT), and a chromatic aberration of magnification (CC) respectively in the close observation state of the example 1.

FIG. 2A and FIG. 2B are diagrams showing a cross-sectional arrangement of the objective optical system. Here, FIG. 2A is a diagram showing a cross-sectional arrangement of the objective optical system in a normal observation state (an object point at a long distance), and FIG. 2B is a diagram showing a cross-sectional arrangement of the objective optical system in a close observation state (an object point at a close distance).

The objective optical system according to the present example includes in order from an object side, a first lens group G1 having a negative refractive power, a second lens group G2 having a positive refractive power, and a third lens group G3 having a positive refractive power. Moreover, an aperture stop S is disposed in the third lens group G3. The second lens group G2 moves toward an image side on an optical axis AX and corrects a change in a focal position due to a change from the normal observation state to the close observation state.

The first lens group G1 includes a planoconcave negative lens L1, a plane-parallel plate L2, a biconcave negative lens L3, and a biconvex positive lens L4. Here, the biconcave negative lens L3 and the biconvex positive lens L4 are cemented.

The second lens group G2 includes a positive meniscus lens L5 having a convex surface directed toward the object side.

The third lens group G3 includes a positive meniscus lens L6 having a convex surface directed toward the image side, a negative meniscus lens L7 having a convex surface directed toward the image side, an aperture stop S, a planoconvex positive lens L8, a biconvex positive lens L9, and a negative meniscus lens L10 having a convex surface directed toward the image side. Here, the positive meniscus lens L6 and the negative meniscus lens L7 are cemented. The biconvex positive lens L9 and the negative meniscus lens L10 are cemented.

An optical path splitting unit 20 is disposed on the image side of the third lens group G3. An optical path is bent in a prism in an optical system. The optical path splitting unit 20 will be described later. The plane-parallel plate L2 is a filter having a coating applied thereon for cutting light of a specific wavelength such as YAG (Yttrium Aluminum Garnet) laser of 1060 nm, semiconductor laser of 810 nm, or light of near-infrared region.

FIG. 3A, FIG. 3B, FIG. 3C, and FIG. 3D show a spherical aberration (SA), an astigmatism (AS), a distortion (DT), and a chromatic aberration of magnification (CC) respectively in the normal observation state of the present example.

FIG. 3E, FIG. 3F, FIG. 3G, and FIG. 3H show a spherical aberration (SA), an astigmatism (AS), a distortion (DT), and a chromatic aberration of magnification (CC) respectively in the close observation state of the present example.

These various aberration diagrams show aberrations at wavelengths of 656.27 nm (C-line), 587.56 nm (d-line), and 435.84 nm (g-line). Moreover, in each diagram, G) denotes a half angle of view. Similar is the case for aberration diagrams described below.

Example 2

An objective optical system in an endoscope system according to an example 2 of the present invention will be described below.

Figure 4A:
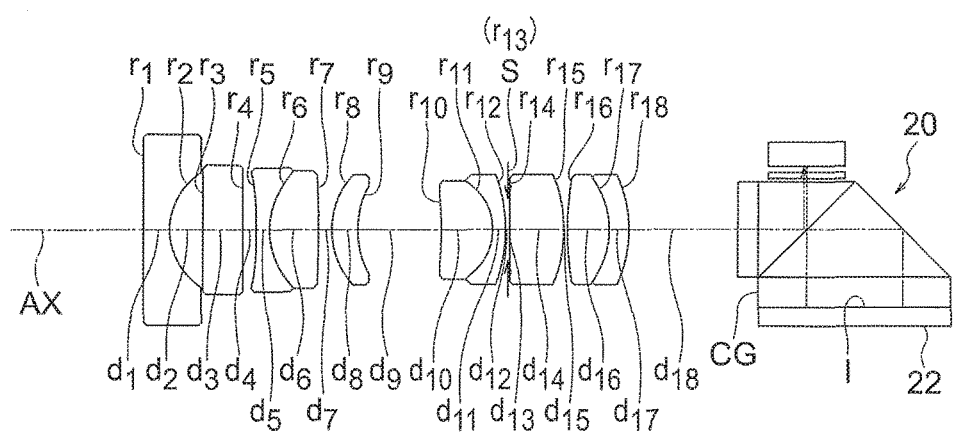
FIG. 4A and FIG. 4B are diagrams showing a cross-sectional arrangement of an objective optical system, an optical path splitting unit, and an image pickup element in an endoscope system according to an example 2 of the present invention, where.
Figure 4B:
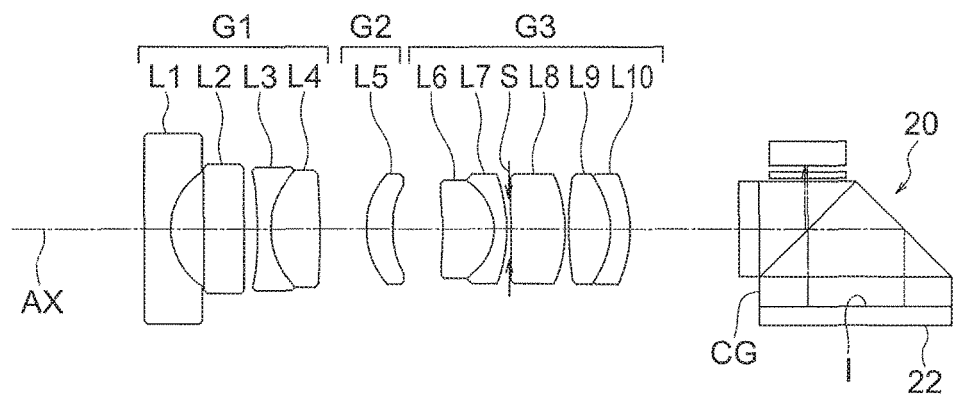

FIG. 4A and FIG. 4B are diagrams showing a cross-sectional arrangement of the objective optical system. Here, FIG. 4A is a diagram showing a cross-sectional arrangement of the objective optical system in a normal observation state (an object point at a long distance), and FIG. 4B is a diagram showing a cross-sectional arrangement of the objective optical system in a close observation state (an object point at a close distance).

The objective optical system according to the present example includes in order from an object side, a first lens group G1 having a negative refractive power, a second lens group G2 having a positive refractive power, and a third lens group G3 having a positive refractive power. Moreover, an aperture stop S is disposed in the third lens group G3. The second lens group G2 moves toward an image side on an optical axis AX and corrects a change in a focal position due to a change from the normal observation state to the close observation state.

The first lens group G1 includes a planoconcave negative lens L1, a plane-parallel plate L2, a biconcave negative lens L3, and a biconvex positive lens L4.

The second lens group G2 includes a positive meniscus lens L5 having a convex surface directed toward the object side.

The third lens group G3 includes a positive meniscus lens L6 having a convex surface directed toward the image side, a negative meniscus lens L7 having a convex surface directed toward the image side, an aperture stop S, a planoconvex positive lens L8, a biconvex positive lens L9, and a negative meniscus lens L10 having a convex surface directed toward the image side. Here, the positive meniscus lens L6 and the negative meniscus lens L7 are cemented. The biconvex positive lens L9 and the negative meniscus lens L10 are cemented.

An optical path splitting unit 20 is disposed on the image side of the third lens group G3. An optical path is bent in a prism in an optical system. The optical path splitting unit 20 will be described later. The plane-parallel plate L2 is a filter having a coating applied thereon for cutting light of a specific wavelength such as YAG laser of 1060 nm, semiconductor laser of 810 nm, or light of near-infrared region.

FIG. 5A, FIG. 5B, FIG. 5C, and FIG. 5D show a spherical aberration (SA), an astigmatism (AS), a distortion (DT), and a chromatic aberration of magnification (CC) respectively in the normal observation state of the present example.

FIG. 5E, FIG. 5F, FIG. 5G, and FIG. 5H show a spherical aberration (SA), an astigmatism (AS), a distortion (DT), and a chromatic aberration of magnification (CC) respectively in the close observation state of the present example.

Example 3

An objective optical system in an endoscope system according to an example 3 of the present invention will be described below.

Figure 6A:
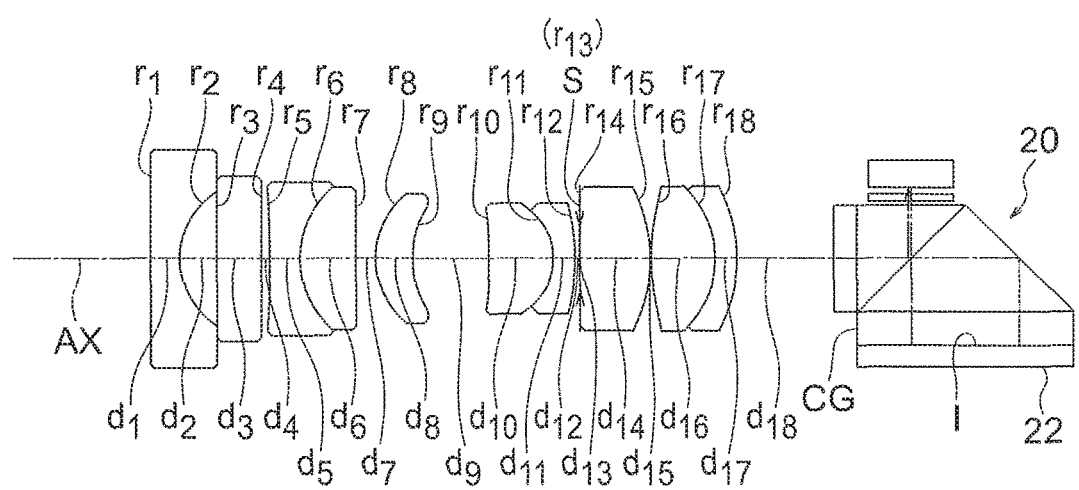
FIG. 6A and FIG. 6B are diagrams showing a cross-sectional arrangement of an objective optical system, an optical path splitting unit, and an image pickup element in an endoscope system according to an example 3 of the present invention, where.
Figure 6B:
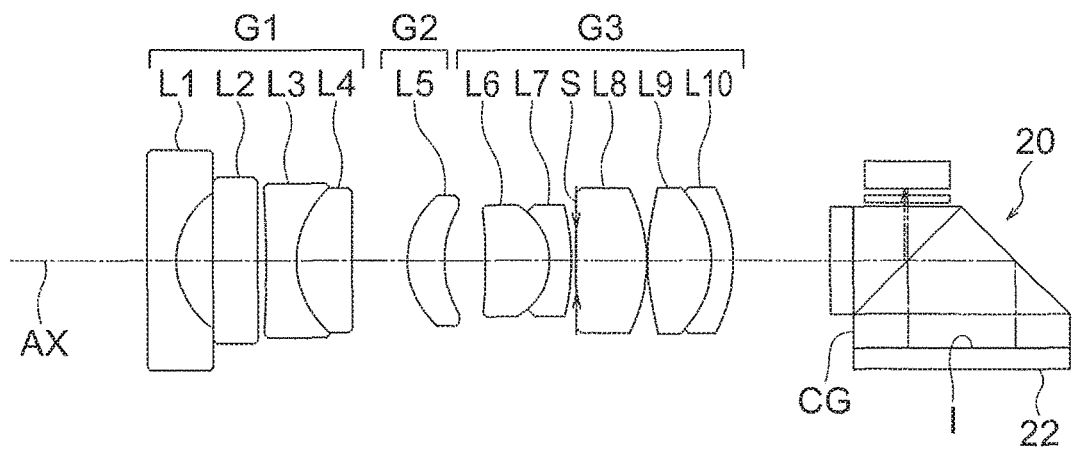

FIG. 6A and FIG. 6B are diagrams showing a cross-sectional arrangement of the objective optical system. Here, FIG. 6A is a diagram showing a cross-sectional arrangement of the objective optical system in a normal observation state (an object point at a long distance), and FIG. 6B is a diagram showing a cross-sectional arrangement of the objective optical system in a close observation state (an object point at a close distance).

The objective optical system according to the present example includes in order from an object side, a first lens group G1 having a negative refractive power, a second lens group G2 having a positive refractive power, and a third lens group G3 having a positive refractive power. Moreover, an aperture stop S is disposed in the third lens group G3. The second lens group G2 moves toward an image side on an optical axis AX and corrects a change in a focal position due to a change from the normal observation state to the close observation state.

The first lens group G1 includes a planoconcave negative lens L1, a plane-parallel plate L2, a biconcave negative lens L3, and a biconvex positive lens L4. Here, the biconcave negative lens L3 and the biconvex positive lens L4 are cemented.

The second lens group G2 includes a positive meniscus lens L5 having a convex surface directed toward the object side.

The third lens group G3 includes a positive meniscus lens L6 having a convex surface directed toward the image side, a negative meniscus lens L7 having a convex surface directed toward the image side, an aperture stop S, a biconvex positive lens L8, a biconvex positive lens L9, and a negative meniscus lens L10 having a convex surface directed toward the image side. Here, the positive meniscus lens L6 and the negative meniscus lens L7 are cemented. The biconvex positive lens L9 and the negative meniscus lens L10 are cemented.

An optical path splitting unit 20 is disposed on the image side of the third lens group G3. An optical path is bent in a prism in an optical system. The optical path splitting unit 20 will be described later. The plane-parallel plate L2 is a filter having a coating applied thereon for cutting light of a specific wavelength such as YAG laser of 1060 nm, semiconductor laser of 810 nm, or light of near-infrared region.

FIG. 7A, FIG. 7B, FIG. 7C, and FIG. 7D show a spherical aberration (SA), an astigmatism (AS), a distortion (DT), and a chromatic aberration of magnification (CC) respectively in the normal observation state of the present example.

FIG. 7E, FIG. 7F, FIG. 7G, and FIG. 7H show a spherical aberration (SA), an astigmatism (AS), a distortion (DT), and a chromatic aberration of magnification (CC) respectively in the close observation state of the present example.

Numerical data for each example is shown below. Regarding symbols, r denotes a radius of curvature of each lens surface, d denotes a distance between two lens surfaces, nd denotes a refractive index about a d-line of each lens, vd denotes Abbe's number for each lens, FNO denotes an F-number, and $\omega$ denotes a half angle of view.

Example 1

Unit mm

Surface data

| Surface no. | r | d | nd | vd |
|---|---|---|---|---|
| 1 | ∞ | 0.44 | 1.88300 | 40.76 |
| 2 | 1.277 | 0.62 | | |
| 3 | ∞ | 0.66 | 1.51800 | 75.00 |
| 4 | ∞ | 0.15 | | |
| 5 | −3.765 | 0.22 | 1.88300 | 40.76 |
| 6 | 1.867 | 0.95 | 1.84666 | 23.78 |
| 7 | −5.648 | Variable | | |
| 8 | 1.479 | 0.44 | 1.48749 | 70.23 |
| 9 | 1.634 | Variable | | |
| 10 | −3.521 | 0.90 | 1.64769 | 33.79 |
| 11 | −0.998 | 0.22 | 1.88300 | 40.76 |
| 12 | −2.573 | 0.06 | | |
| 13(Stop) | ∞ | 0.00 | | |
| 14 | ∞ | 0.93 | 1.48749 | 70.23 |
| 15 | −2.659 | 0.06 | | |
| 16 | 5.794 | 0.67 | 1.48749 | 70.23 |
| 17 | −1.567 | 0.33 | 1.92286 | 18.90 |
| 18 | −2.318 | 3.94 | | |
| 19(Imaging surface) | ∞ | | | |

Zoom data

| | Normal observation state | Close observation state |
|---|---|---|
| focal length | 0.73 | 0.73 |
| Fno. | 3.58 | 3.52 |
| Angle of view 2ω | 136.30 | 133.76 |
| d7 | 0.22 | 1.12 |
| d9 | 1.78 | 0.88 |

Group focal length

| f1 = −1.29 | f2 = 16.55 | f3 = 2.51 |
|---|---|---|

Example 2

Unit mm

Surface data

| Surface no. | r | d | nd | vd |
|---|---|---|---|---|
| 1 | ∞ | 0.41 | 1.88300 | 40.76 |
| 2 | 1.148 | 0.52 | | |
| 3 | ∞ | 0.62 | 1.00000 | 65.13 |
| 4 | ∞ | 0.21 | | |
| 5 | −5.040 | 0.21 | 1.88300 | 40.76 |
| 6 | 1.370 | 0.78 | 1.84666 | 23.78 |
| 7 | −10.799 | Variable | | |
| 8 | 1.394 | 0.41 | 1.48749 | 70.23 |
| 9 | 1.623 | Variable | | |
| 10 | −4.845 | 0.83 | 1.64769 | 33.79 |
| 11 | −0.940 | 0.21 | 1.88300 | 40.76 |
| 12 | −2.618 | 0.06 | | |
| 13(Stop) | ∞ | 0.00 | | |
| 14 | ∞ | 0.87 | 1.48749 | 70.23 |
| 15 | −2.246 | 0.06 | | |
| 16 | 5.696 | 0.67 | 1.48749 | 70.23 |
| 17 | −1.477 | 0.31 | 1.92286 | 18.90 |
| 18 | −2.201 | 3.62 | | |
| 19(Imaging surface) | ∞ | | | |

Zoom data

| | Normal observation state | Close observation state |
|---|---|---|
| focal length | 0.71 | 0.71 |
| Fno. | 3.54 | 3.49 |
| Angle of view 2ω | 144.97 | 141.76 |
| d7 | 0.21 | 0.75 |
| d9 | 1.32 | 0.78 |

Group focal length

| f1 = −1.05 | f2 = 12.66 | f3 = 2.30 |
|---|---|---|

Example 3

| Unit mm | | | | |
|---|---|---|---|---|
| Surface data | | | | |
| Surface no. | r | d | nd | vd |
| 1 | ∞ | 0.41 | 1.88300 | 40.76 |
| 2 | 1.187 | 0.52 | | |
| 3 | ∞ | 0.60 | 1.51800 | 75.00 |
| 4 | ∞ | 0.13 | | |
| 5 | −10.716 | 0.42 | 1.88300 | 40.76 |
| 6 | 1.435 | 0.79 | 1.84666 | 23.78 |
| 7 | −25.907 | Variable | | |
| 8 | 1.280 | 0.52 | 1.48749 | 70.23 |
| 9 | 1.504 | Variable | | |
| 10 | −6.016 | 0.91 | 1.64769 | 33.79 |
| 11 | −0.915 | 0.31 | 1.88300 | 40.76 |
| 12 | −3.148 | 0.06 | | |
| 13(Stop) | ∞ | 0.00 | | |
| 14 | 43.657 | 1.00 | 1.48749 | 70.23 |
| 15 | −2.302 | 0.03 | | |
| 16 | 3.834 | 0.91 | 1.48749 | 70.23 |
| 17 | −1.454 | 0.31 | 1.92286 | 18.90 |
| 18 | −2.191 | 3.22 | | |
| 19(Imaging surface) | ∞ | | | |

| Zoom data | | |
|---|---|---|
| | Normal observation state | Close observation state |
| focal length | 0.72 | 0.72 |
| Fno. | 3.58 | 3.52 |
| Angle of view 2ω | 144.52 | 141.51 |
| d7 | 0.26 | 0.79 |
| d9 | 1.08 | 0.55 |

| Group focal length | | |
|---|---|---|
| f1 = −1.16 | f2 = 10.01 | f3 = 2.21 |

Values of the conditional expressions (1) to (7) of example 1, example 2 and example 3 are shown below.

| Conditional | | | |
|---|---|---|---|
| | Example1 | Example2 | Example3 |
| Expression | | | |
| (1) D_diff/im_pitch | 3.333 | 25.000 | 100.000 |
| (2) D_diff/R1_r | 0.008 | 0.044 | 0.084 |
| (3) D_diff/R1_f | 0.000 | 0.000 | 0.000 |
| (4) D_diff/FL_L01 | −0.007 | −0.039 | −0.075 |
| (5) D_diff/fw | 0.0136 | 0.0702 | 0.1386 |
| (6) D_diff/FB | 0.003 | 0.014 | 0.031 |
| (7) ω(w)/ω(t) | 1.019 | 1.024 | 1.015 |
| Parameter | | | |
| D_diff | 0.01 | 0.05 | 0.1 |
| im_pitch | 0.003 | 0.002 | 0.001 |
| R1_r | 1.2771 | 1.1482 | 1.1868 |
| R1_f | ∞ | ∞ | ∞ |
| FL_L01 | −1.4379 | −1.2928 | −1.3363 |
| fw | 0.7328 | 0.7126 | 0.7214 |
| FB | 3.94 | 3.6196 | 3.225 |
| ω(w) | 68.558 | 73.325 | 63.371 |
| ω(t) | 67.26 | 71.638 | 62.406 |

(Embodiment of Endoscope System)

Next, an endoscope system which includes the abovementioned objective optical system will be described below.

Figure 9:
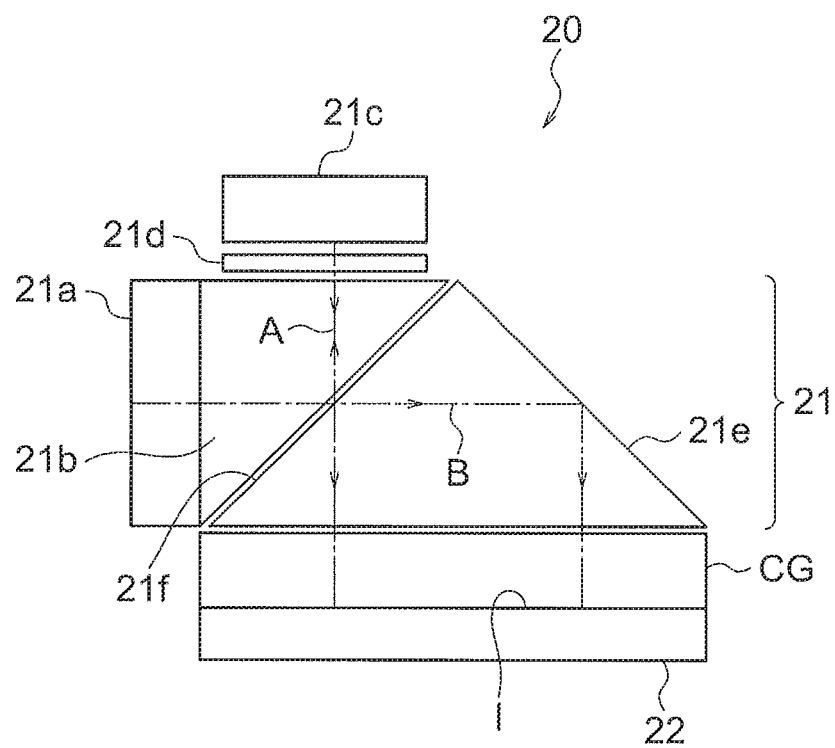
FIG. 9 is a schematic block diagram of an optical path splitting unit and an image pickup element in the endoscope system according to the embodiment of the present invention.

FIG. 8 is a function block diagram of an endoscope system 10. FIG. 9 is a diagram showing a schematic arrangement of the optical path splitting unit 20.

Light emerged from an objective optical system OBL of each of the abovementioned example is incident on the optical path splitting unit 20.

The optical path splitting unit 20 includes a polarization beam splitter 21 which splits an object image into two optical images of different focus, and an image pickup element 22 which acquires two images by capturing two optical images.

The polarization beam splitter 21, as shown in FIG. 9, includes a first prism 21b, a second prism 21e, a mirror 21c, and a λ/4 plate 21d. Both the first prism 21b and the second prism 21e have a beam-splitting surface which is inclined at 45 degrees with respect to an optical axis.

A polarization splitting film 21f is formed on the beam splitting surface of the first prism 21b. The polarization beam splitter 21 is formed by letting the beam splitting surfaces of the first prism 21b and the second prism 21e respectively make a mutual contact via the polarization splitting film 21f.

Moreover, the mirror 21c is provided near an end surface of the first prism 21b via the λ/4 plate 21d. The image pickup element 22 is attached to an end surface of the second prism 21e via a cover glass CG.

An object image from the objective optical system OBL is split into a P-polarization component (light transmitted) and an S-polarization component (light reflected) by the polarization splitting film. 21f provided to the beam splitting surface in the first prism 21b, and is split into two optical images namely an optical image on a side of the light reflected and an optical image on a side of the light transmitted.

The optical image of the S-polarization component, upon being reflected at the polarization splitting film 21f toward a side of a surface facing the image pickup element 22 follows an optical path A, and after being transmitted through the λ/4 plate 21d, is reflected at the mirror 21c and returned toward the image pickup element 22. The optical image returned has an angle of polarization turned through 90° by being transmitted once again through the λ/4 plate 21d, and is transmitted through the polarization splitting film 21f and is formed on the image pickup element 22.

The optical image of the P-polarization component, upon being transmitted through the polarization splitting film 21f, follows an optical path B, and is reflected by a mirror surface provided to a side facing the beam splitting surface of the second prism 21e that returns perpendicularly toward the image pickup element 22, and is formed on the image pickup element 22. At this time, path in prism glass is set to generate a predetermined optical path difference of a few tens of μm in the optical path A and the optical path B, and two optical images of different focus are formed on a light-receiving surface of the image pickup element 22.

In other words, the first prism 21b and the second prism 21e are to be disposed such that, an optical path length on the side of the light reflected becomes short (small) with respect to an optical path length (path length in glass) on the side of the light transmitted reaching the image pickup element 22 in the first prism 21b in order to be able to split the object image into two optical images of different focusing positions.

Figure 10:
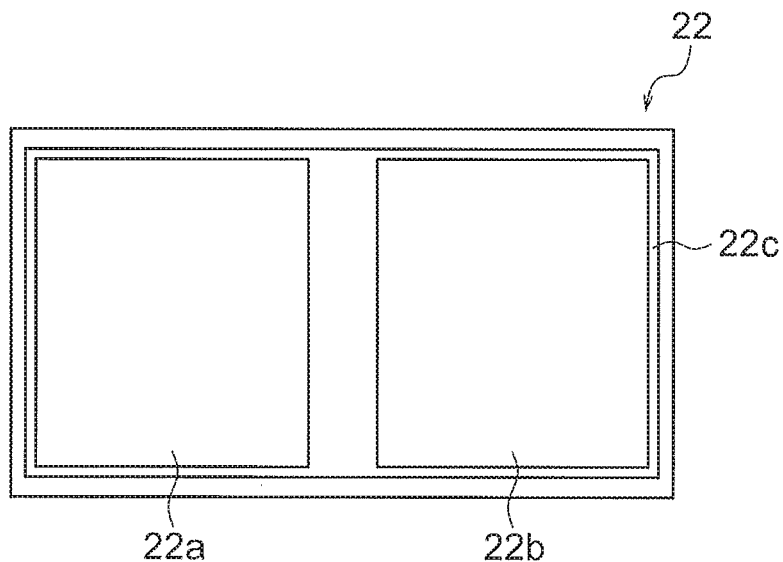
FIG. 10 is a schematic block diagram of the image pickup element in the endoscope system according to the embodiment of the present invention.

The image pickup element 22, as shown in FIG. 10, is provided with two light-receiving areas (effective pixel areas) 22a and 22b in a total pixel area of the image pickup element 22 for receiving and capturing separately the two optical images of different focusing positions.

The light-receiving areas 22a and 22b are disposed to coincide with image formation surfaces of these optical images respectively. Moreover, in the image pickup element 22, the focusing position of the light-receiving area 22a with respect to the light-receiving area 22b is shifted relatively toward a near-point side, and the focusing position of the light receiving area 22b with respect to the light-receiving area 22a is shifted relatively toward a far-point side. Accordingly, an arrangement is made to form two optical images of different focus on the light-receiving surface of the image pickup element 22.

By letting a refractive index of glass materials of the first prism 21b and the second prism 21e to be different, the optical path length reaching the image pickup element 22 may be changed, and the focusing positions for the light-receiving areas 22a and 22b may be shifted relatively.

Moreover, a correction pixel area 22c for correcting a geometrical shift of the optical image divided into two is provided around the light-receiving areas 22a and 22b. By suppressing a manufacturing error in the correction pixel area 22c, and carrying out the correction by image processing in an image correction processing section 23b (FIG. 8) that will be described later, the geometrical shift of the optical image is eliminated.

The second lens group G2 in each of the abovementioned examples is a focusing lens and can be moved selectively to two positions in a direction of an optical axis. The second lens group G2 is moved by an actuator which is not shown in the diagram to the two positions from one position to the other position and from the other position to the one position.

The setting is to be carried out such that an object in an observation area, in a case of making a distant observation (normal observation) in a state in which the second lens group G2 is set at a front-side (object side) position, is in focus. Moreover, the setting is to be carried out such that an object in an observation area, in a case of making a close observation (magnifying observation) in a state in which the second lens group G2 is set at a rear-side position is in focus.

As in the present embodiment, in a case of carrying out polarization splitting by using the polarization beam splitter 21, when a polarization state of light to be split is not circularly-polarized light, there arises a difference in brightness of images split. Correction of an orderly difference in brightness by image processing is comparatively easy, but when the difference in brightness arises locally and according to observation conditions, it cannot be corrected fully, and in some cases, this leads to an unevenness in brightness in a composite image.

For an object to be observed by an endoscope, there is a possibility of unevenness in brightness in a comparatively peripheral portion of the field of view of the composite image. This unevenness in brightness due to a disrupted polarization state appears remarkably when the object has a brightness distribution that tends to be saturated comparatively.

In the peripheral portion of the field of view, a blood stream or mucosal structure of an object image is to be viewed comparatively closely in an endoscope in a large number of cases, and a possibility of an image becoming extremely complicated for a user is high.

Therefore, as shown in FIG. 9 for instance, it is preferable to dispose the λ/4 plate 21a on the object side of the optical path splitting unit 20 than the polarization splitting film 21f in order to restore the disturbed polarization state to the circularly-polarized light.

A half mirror which splits intensity of light incident can also be used instead of the abovementioned polarization beam splitter.

Next, a combining of two images acquired will be described below by referring to FIG. 8.

An image processor 23 includes an image reading section 23a which reads images related to the two optical images with different focusing positions captured by the image pickup element 22, the image correction processing section 23b which carries out image correction for two images read by the image reading section 23a, and an image synthesis processing section 23c which carries out image synthesis processing of combining the two images corrected.

The image correction processing section 23b carries out correction of the images related to the two optical images formed in the light-receiving areas 22a and 22b respectively of the image pickup element 22 such that mutual differences other than the focus becomes substantially same for the two images. In other words, the image correction processing section 23b carries out correction of the two images such that relative position, angle, and magnification of each optical image of the two images are substantially same.

In a case of splitting the object image into two and forming each image on the image pickup element 22, a geometrical difference is generated in some cases. In other words, the optical images formed on the light-receiving surfaces 22a and 22b respectively of the image pickup element 22 have a relative shift in magnification, shift in position, shift in angle, and shift in direction of rotation in some cases.

It is difficult to completely eliminate these differences at the time of manufacturing, and when an amount of shift becomes large, the composite image becomes a double image giving rise to unusual unevenness in brightness. Therefore, the abovementioned geometrical difference and difference in brightness are to be corrected in the image correction processing section 23b.

In a case of correcting the difference in brightness between the two images, it is desirable to carry out the correction with reference to an image or a screen image having a low luminance out of the two images or screen images, or an image or a screen image having a low luminance at relatively same position out of the two images or screen images.

The image synthesis processing section 23c, in a corresponding predetermined area between the two images corrected by the image correction processing section 23b, selects an image with a relatively high contrast, and generates a composite image. In other words, the image synthesis processing section 23c compares the contrast in each of the spatially same pixel area in the two images, and by selecting a pixel area with relatively high contrast, generates a composite image as one image having the two images combined.

In a case in which, a difference in contrast in the same pixel area of the two images is small or the contrast is substantially same, by a synthesis image processing of calculating upon predetermined weighting of that pixel area, a composite image is generated.

Moreover, the image processor 23, for one image combined by the image synthesis processing section 23c, carries out a post-stage image processing such as a color matrix processing, an outline enhancement, and a gamma correction processing. An image output section 23d outputs an image subjected to the post-stage image processing. An image output from the image output section 23d is output to an image display section 24.

Moreover, the relative focusing positions may be let to be shifted by forming the first prism 21b and the second prism 21e of a different glass material depending on whether the optical path reaching the image pickup element is a near-point optical path or a far-point optical path, and letting the refractive indices to differ.

Accordingly, images related to two optical images of different focus are acquired, and by combining these images by the image synthesis processing section 23c, it is possible to obtain a combined depth of field. For screening upon taking a long shot of a wide range in endoscopy, the distant observation is suitable, and for observing details of a lesion, and diagnosis, the close observation is suitable.

By adopting such an arrangement, it is possible to widen the depth of field without letting the resolving power to be degraded even when an image pickup element with even larger number of pixels is used. Furthermore, since there is a focusing mechanism, it is possible to carry out endoscopic observation with a high-quality image by switching the range of observation flexibly, and diagnosis.

Figure 11:
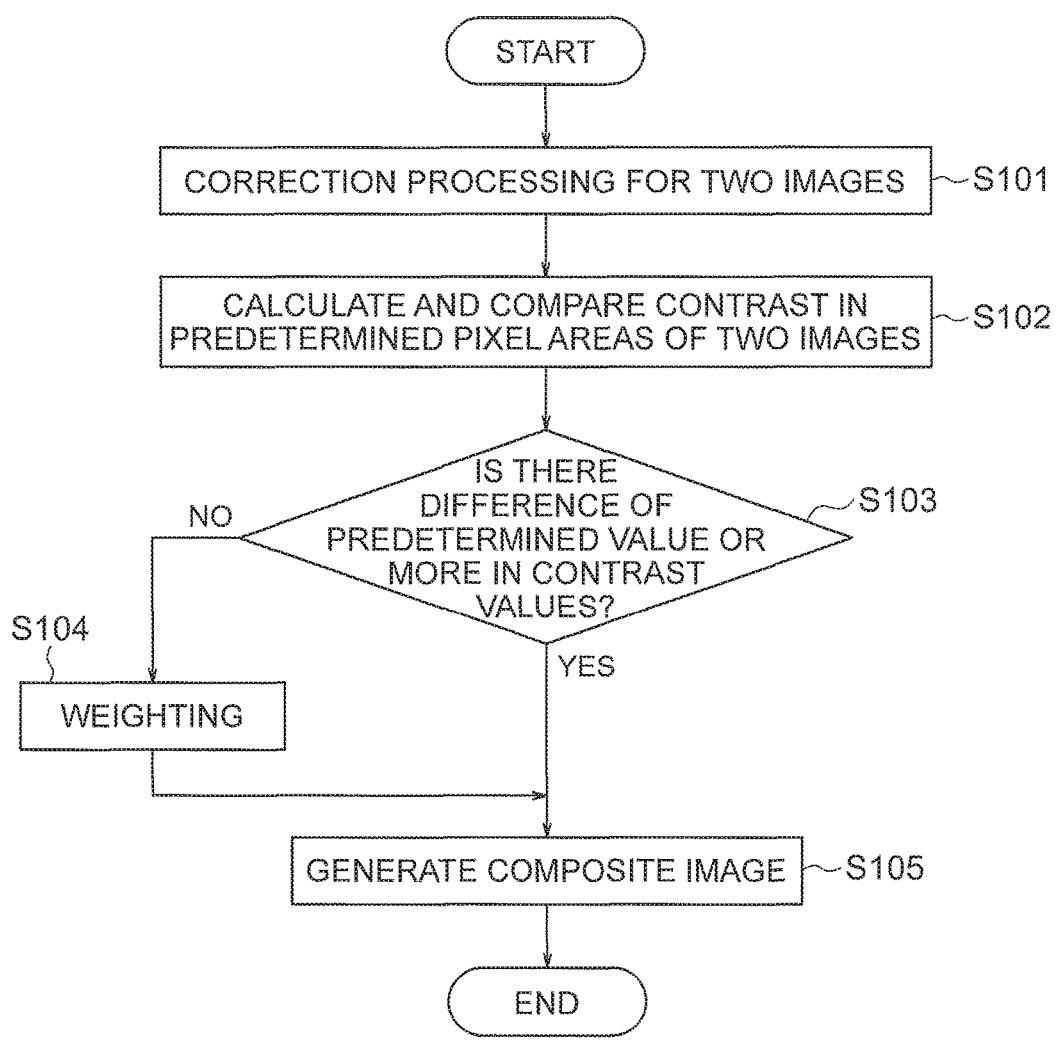
FIG. 11 is a flowchart showing a flow in a case of combining two optical images in the endoscope system according to the embodiment of the present invention.

Next, a flow in a case of combining the two optical images in the present embodiment will be described below while referring to a flowchart in FIG. 11.

At step S101, an image related to a far-point image and an image related to a near-point image of different focus acquired by the image pickup element 22 are subjected to correction processing of two near and far images in the image correction processing section 23b. In other words, according to correction parameters that have been set in advance, correction of two images is carried out such that the relative positions, angles, and magnification of optical images of the two images become substantially same, and images, after being subjected to correction, are output to the image synthesis processing section 23c. A difference in brightness and color of the two images may be corrected if necessary.

At step S102, the two images subjected to correction processing are combined in the image synthesis processing section 23c. At this time, contrast values for the pixel areas corresponding to the two near and far images respectively are calculated and compared.

At step S103, a judgment of whether or not there is a difference in the contrast values compared is made, and in a case in which there is a difference in the contrast values, the process advances to step S105, and the images are combined upon selecting an area of a high contrast value.

Here, in a case in which, the difference in the contrast values compared is small or the contrast values are almost same, as to which of the two near and far images is to be selected becomes a factor of uncertainty in processing. For instance, when there is a fluctuation of signal such as noise, there occurs a discontinuous area in the composite image, which leads to a trouble such as blurring of the object image which would have been resolved originally.

Therefore, the process advances to step S104, and weighting is carried out. At step S104, in a case in which, the contrast values for the two images are almost same in the pixel areas for which the comparison of contrast has been carried out, the weighting is carried out, and the uncertainty of image selection is eliminated by carrying out an adding processing of image subjected to weighting at the subsequent step S105.

Thus, according to the present embodiment, in both the close observation and the distant observation, it is possible to acquire an image in which the depth of field is widened while preventing an occurrence of the discontinuous area in the composite image due to noise, and preventing the optical image from being blurred.

Moreover, since the two images are captured by the same image pickup element, it is possible to reduce a manufacturing cost as compared to a case in which a plurality of image pickup elements is used, and to acquire an image in which the depth of field is widened without the apparatus becoming large.

Moreover, the desired depth of field is achieved and it is possible to prevent degradation of resolving power.

In a case of the abovementioned polarization beam splitter 21 of FIG. 9, an optical image is formed on the image pickup element 22 after one reflection or in other words, after odd number of reflections. Therefore, any one of the images is formed as an image (mirror-image) shown in FIG. 12, and an image processing of making a direction of images coincide by inverting the mirror-image in the image processor 23 is to be carried out.

Since the correction of a mirror-image by even number of optical reflections sometimes leads to making an objective system large-sized and a prism cost high, it is preferable to carry out the correction of mirror-image by odd number of reflections by inverting the mirror-image in the image correction processing section 23b.

In a case in which the image pickup element 22 has a shape which is long in a longitudinal direction of endoscope, it is preferable to rotate the composite image appropriately upon taking into consideration an aspect ratio of the image display section 24.

Various embodiments of the present invention have been described heretofore. However, the present invention is not limited only to the embodiments described above, and embodiments in which arrangements of these embodiments have been combined appropriately without departing from the scope of the invention are also within the scope of the present invention.

As described heretofore, the present invention is useful for an endoscope system in which, the depth of field is widened, and which is capable of achieving a high-quality image with an aberration corrected favorably.

An endoscope system according to an embodiment of the present invention shows an effect that it is possible to achieve a high-quality image with an aberration corrected favorably, and the depth of field widened.

The invention claimed is:

1. An endoscope system, comprising:
an objective optical system;
a beam splitter which splits reflected light and transmitted light components of an object image acquired by the objective optical system into two optical images of different focus;
an image pickup element which acquires the two optical images; and
a processor comprising hardware, the processor being configured to:
select, in a predetermined area, an image with a relatively high contrast from among the two optical images acquired; and
generate a composite image,
wherein:
the objective optical system includes a first lens having a negative refractive power which is nearest to an object of observation, and
the endoscope system satisfies the following conditional expressions (1) and (2):

$$3 < D\_diff/im\_pitch < 100 \qquad (1), \text{and}$$

$$0.005 < D\_diff/R1\_r < 1.0 \qquad (2),$$

where:
D_diff denotes a difference in length of optical paths of the two optical images from a splitting position to a surface of the image pickup element, the difference being between equivalent optical paths in air of the optical paths, im_pitch denotes a pixel pitch of the image pickup element, and R1_r denotes a radius of curvature at an image-side surface of the first lens.

2. The endoscope system according to claim 1, wherein the endoscope system further satisfies the following conditional expressions (3) and (4):

$$-0.05 < D\_diff/R1\_f < 0.05 \quad (3), \text{ and}$$

$$-1.0 < D\_diff/FL\_L01 < -0.005 \quad (4),$$

where:
R1_f denotes a radius of curvature at an object-side surface of the first lens, and FL_L01 denotes a focal length of the first lens.

3. The endoscope system according to claim 1, wherein the endoscope system further satisfies the following conditional expressions (5) and (6):

$$0.01 < D\_diff/fw < 2.0 \quad (5), \text{ and}$$

$$0.002 < D\_diff/FB < 0.05 \quad (6),$$

where:
fw denotes a focal length of the objective optical system, and

FB denotes an equivalent optical path in air of an optical path from a rearmost lens of the objective optical system up to an image forming position.

4. The endoscope system according to claim 1, wherein:
the objective optical system enables normal observation and close observation by driving a lens at an interior of the objective optical system, and the endoscope system further satisfies the following conditional expression (7):

$$1.01 < \omega(w)/\omega(t) < 2.0 \quad (7),$$

where:
$\omega(w)$ denotes a half angle of view at a time of normal observation of the objective optical system, and $\omega(t)$ denotes a half angle of view at a time of close observation of the objective optical system.

* * * * *

UNITED STATES PATENT AND TRADEMARK OFFICE
CERTIFICATE OF CORRECTION

PATENT NO. : 9,949,622 B2
APPLICATION NO. : 15/342414
DATED : April 24, 2018
INVENTOR(S) : Masahiro Katakura et al.

Page 1 of 1

It is certified that error appears in the above-identified patent and that said Letters Patent is hereby corrected as shown below:

In the Specification

Column 7, Line 54, delete "G)" and insert --ω--.

In the Claims

Column 16, Line 65, Claim 1, Line 21, delete "<100" and insert --≤100--.

Signed and Sealed this
Twenty-first Day of August, 2018

Andrei Iancu
*Director of the United States Patent and Trademark Office*